(12) United States Patent  (10) Patent No.: US 7,879,594 B2
Mandrand et al.  (45) Date of Patent: Feb. 1, 2011

(54) METHOD AND DEVICE FOR DETECTING BIOMOLECULES

(75) Inventors: Bernard Mandrand, Villeurbanne (FR); Agnes Dupont-Filliard, Les Adrets (FR)

(73) Assignee: Biomerieux, Marcy l'Etoile (FR)

( * ) Notice: Subject to any disclaimer, the term of this patent is extended or adjusted under 35 U.S.C. 154(b) by 1055 days.

(21) Appl. No.: 10/548,869

(22) PCT Filed: Mar. 15, 2004

(86) PCT No.: PCT/EP2004/002685

§ 371 (c)(1), (2), (4) Date: Jun. 14, 2006

(87) PCT Pub. No.: WO2004/081566

PCT Pub. Date: Sep. 23, 2004

(65) Prior Publication Data

US 2007/0037153 A1  Feb. 15, 2007

(30) Foreign Application Priority Data

Mar. 14, 2003 (DE) .............................. 103 11 315

(51) Int. Cl.
*C12M 1/00* (2006.01)
(52) U.S. Cl. .................. 435/287.2; 435/7.1; 435/283.1; 436/518; 436/524; 436/525; 977/700; 977/702; 977/704; 977/705; 977/720
(58) Field of Classification Search .............. 435/6, 435/7.1, 7.5, 7.9, 7.92, 283.1, 287.2; 436/518, 436/524, 525; 422/50, 68.1, 78, 82.01; 977/700, 977/702, 704, 705, 720, 904, 920
See application file for complete search history.

(56) References Cited

U.S. PATENT DOCUMENTS 5,202,261 A  4/1993  Musho et al.

(Continued)

FOREIGN PATENT DOCUMENTS

EP  0408578  1/1991

(Continued)

OTHER PUBLICATIONS

H. Zhao "Study on the Formation of the Prussian Blue Films on the Polypyrrole Surface as Potentional Mediator System for Biosensing Applications" Apr. 12, 2002.

(Continued)

*Primary Examiner*—Melanie Yu
(74) *Attorney, Agent, or Firm*—Millen, White, Zelano & Branigan, P.C.

(57) ABSTRACT

The present invention relates to a method for detecting a target biomolecule in a sample comprising a plurality of biomolecules, whereby the target biomolecule is provided with a tag, said tag comprising a catalytic active moiety which catalyses a reaction yielding an insoluble reaction product which precipitates on flexible electrically conductive nanoelectrodes. The precipitation onto said nanoelectrodes causes a change in their electroconductivity which is accessible to electroanalytical methods. The invention relates further to a biochip comprising a solid support with nanoelectrodes attached thereto and probe molecules bound to all or to a plurality of said nanoelectrodes which may be the same or different, a segment of said probe molecules being able to interact specifically with a segment of the target biomolecules.

19 Claims, 8 Drawing Sheets

U.S. PATENT DOCUMENTS

| | | | |
|---|---|---|---|
| 5,364,797 A * | 11/1994 | Olson et al. | 436/501 |
| 6,055,106 A | 4/2000 | Grier et al. | |
| 6,096,825 A | 8/2000 | Garnier | |
| 6,123,819 A | 9/2000 | Peeters | |
| 6,342,359 B1 * | 1/2002 | Lee et al. | 435/6 |
| 6,355,429 B1 | 3/2002 | Nygren et al. | |
| 6,869,671 B1 * | 3/2005 | Crouse et al. | 428/304.4 |
| 2002/0172963 A1 * | 11/2002 | Kelley et al. | 435/6 |
| 2003/0148335 A1 * | 8/2003 | Shen et al. | 435/6 |
| 2004/0016035 A1 * | 1/2004 | Floyd | D24/225 |
| 2004/0023258 A1 | 2/2004 | Patolsky et al. | |
| 2004/0080363 A1 | 4/2004 | Gruber et al. | |
| 2005/0112544 A1 * | 5/2005 | Xu et al. | 435/4 |
| 2005/0244863 A1 * | 11/2005 | Mir | 435/6 |

FOREIGN PATENT DOCUMENTS

| | | |
|---|---|---|
| WO | WO 9924823 | 5/1999 |
| WO | WO 0077523 | 12/2000 |
| WO | WO 0106002 | 1/2001 |
| WO | WO 0220838 | 3/2002 |
| WO | WO 02074988 | 9/2002 |
| WO | WO 03012410 | 2/2003 |

OTHER PUBLICATIONS

Hafsa Korri-Youssoufi et al. "Electrochemical Biosensing of DNA Hybridization by Ferrocenyl Groups Functionalized Polypyrrole" Aug. 6, 3001.

* cited by examiner

Figur 3

Figur 3a

Figur 3b

FIGUR 4

FIGUR 5

FIGUR 6

FIGUR 7

FIGUR 8

FIGUR 9

FIGUR 10

FIGUR 11

FIGUR 12a

FIGUR 12b

METHOD AND DEVICE FOR DETECTING BIOMOLECULES

The present invention relates to a method for detecting target biomolecules in samples comprising a plurality of biomolecules and a system for detecting such biomolecules.

The detection of biomolecules for example genetic material of pathogens or nucleic acid sequences for the detection of infectious diseases, genetic and cancer screening has become more and more important in recent biochemistry and medical research.

For example, methods using nucleic acid based probes offer several advantages over conventional microbiological or immunological methods for the detection of organisms as described by Nakamura and Bulund (J. Clinical Laboratory Analysis, 6, 73-83, 1992).

Most of the known methods in prior art rely on the detection of signals generated after hybridization of the nucleic acid probe, for example after various amplification schemes such as polymerase chain reaction (PCR), ligase chain reaction (LCR), transcription based amplification, cycling probe reaction etc.

The probe or hybridization assays are often based on the attachment of an oligonucleotide probe to a surface in order to capture a target nucleic acid molecule from a sample. The attachment of this probe to the surface is accomplished by the formation of covalent bonds or by a variety of passive absorption mechanisms. The immobilized probe is capable of interacting specifically with target molecules, for example with nucleic acid sequences in solution. The interaction and subsequent hybridization allows the detection of the target via different methods.

U.S. Pat. No. 6,355,429 discloses an optical device for determining the presence of a first nucleic acid in a sample comprising a second nucleic acid complementary to the first nucleic acid and which is able to hybridize with the first nucleic acid under hybridizing conditions, the second nucleic acid being immobilized on a solid support, wherein the solid support is formed with a light reflecting surface wherein the hybridization of said sample with the target nucleic acid leads to a change in the light reflective properties which are used as a means for detecting the presence of said target nucleic acids in the sample. The final assay step in changing the optical properties of said surface is carried out by precipitating an enzyme substrate which will deposit large molecules onto the surface by an enzyme dependent reaction. The precipitation results in a visible colour change from gold to purple which can be detected by optical measurement methods.

U.S. Pat. No. 6,096,825 discloses the use of electrically conductive and electro-active functionalized conjugated polypyrrole polymer films which can be linked to a first biological molecule. These polypyrrole films are electrically conductive and form a planer electrode. The so attached first biological molecule can be used to assay for, detect and/or extract a second biological molecule which is able to specifically interact with said first biological molecule, thereby changing the overall conductivity of the "polymer electrode". A major drawback of the method is that the modification of the electrochemical response with respect to a reference polymer has to be in such a magnitude that the overall sensitivity of such a biochip is considerably decreased. The sensitivity of these biochips is limited to the order of $>10^{11}$ molecules/ml.

WO 02/20838 discloses a method and a system for detecting nucleic acid sequences in samples containing a mixture of nucleic acids. On a surface, comprising a plurality of metallic electrodes, a probe comprising an oligonucleotide which is complementary to a segment of the target nucleic acid is attached to a metallic electrode, and a sample subsequently contacted with the surface where the oligonucleotide is bound to, thereby allowing the probe to bind to the target nucleic acid, followed by incubation of the bound target nucleic acid with four nucleotide types and a replication biocatalyst, forming a multi-stranded nucleic acid assembly, wherein at least one of the nucleotide types is bound by a label and detecting the label on the multi-stranded nucleic acid assembly, thereby indirectly detecting the target nucleic acid. The detection is accomplished via an enzyme action on substrates, which act as a redox couple and will precipitate on the metallic electrode whose electronic conductivity is decreased.

A major drawback of this method is the incubation of the bound target nucleic acid with four different nucleotide types and the replication biocatalyst thus leading to unnecessary complication of the detection step. Further disadvantages result from the limitation of the method to nucleic acids only. Biopolymers, different from nucleic acids, like e.g. proteins, peptides, antibodies and the like cannot be used in this method. Furthermore, the metallic electrode according to WO 02/20838 is a planar "two-dimensional" electrode.

It was therefore an object of the present invention to provide a reliable and flexible method with high sensitivity for the optimized detection of biomolecules in samples.

The problem is solved by a method for detecting a target biomolecule in a sample comprising a plurality of biomolecules, whereby the target biomolecule is provided with a tag, said tag comprising a catalytic active moiety which catalyses upon reaction the transformation of an additional soluble species to an insoluble precipitate, said method comprising the steps of:
  a) providing a solid support with a plurality of spatially different locations arranged on its surface, whereby at least one location is electrically conducting and a plurality of individual flexible nanoelectrodes with probe biomolecules attached thereto being linked to said location,
  b) bringing the sample in contact with the solid support comprising said probe biomolecules, thereby forming a recognition complex between a probe biomolecule and a target biomolecule,
  c) adding an essentially soluble species,
  d) transforming the soluble species into an insoluble precipitate forming a deposit essentially on or at the nanoelectrodes, thereby decreasing the flexibility of the nanoelectrodes
  e) measuring the electrical conductivity of the plurality of the nanoelectrodes at at least one location.

The term "flexible nanoelectrode" means within the context of the present invention, that the nanoelectrodes are flexible in itself, i.e. that they are not rigid, and have a certain mobility even after fixation on the location. The nanoelectrodes can for example be best described as individual filaments. It is understood that the length of the nanoelectrodes is in the nanometer range, of from 3 to 500 nm. Preferably, the nanoelectrodes consist of molecular assemblies.

The precipitate can be electrically insulating or electrically conducting as well. An essentially electrically insulating precipitate is preferred. One of the essential functions of the precipitate is to block the flexibility/mobility of the nanoelectrodes which influence the conductivity of the nanoelectrodes.

The molecular assemblies which form the nanoelectrodes consists preferably of electrically conducting polymer chains like substituted or non-substituted polypyrroles, polythiophenes, polytetrahydrofuranes, polyanilines etc. and copolymers thereof. Further, one or a plurality of electron donor moieties (EDM) are attached thereto. The EDM's are preferably transition metal complexes for example transition metal complexes of Fe, Ru, Co, Ni, Pt, Pd, Cn and the like with various σ and π donor ligands, examples of such ligands comprise but are not limited to nitrogen, sulfur and oxygen donor ligands as for example phenanthroline, phthalocyanines, porphyrins, porphyrinogens, calixarenes, bipyridine, further to cyclopentadiene, benzene pyridine and similar π donor ligands. Preferred are sandwich complexes, more preferred metallocenes like ferrocene, ruthenocene, nickelocene and the like. The electrical response of the EDM's is more precise than the response of the polymer and is strongly influenced and modulated by the deposit.

Each polymer chain constitutes a "nanoelectrode" in itself. The electrical conductivity of the polymer chains is correlated with their flexibility/mobility. The length of the polymer chain may vary in the range of 20-300 nm, preferably from 30-200 nm and most preferred from 90-180 nm. Surprisingly, the method according to the invention allows to establish a correlation between the flexibility and mobility of the nanoelectrodes and their conductivity. This correlation, i.e. the change in electrical conductivity, is accessible to various electrical measurement methods as explained in the following. Thus, the deposit of the insoluble precipitate leads to a change in the conductivity of the nanoelectrodes which indicates the formation of a recognition complex between the probe biomolecules and the target biomolecules.

The method according to the invention enables the detection of target biomolecules with a sensitivity of $<10^8$ molecules/ml. In one embodiment steps a) and b) will take place at the same time (i.e. synthesis of the polymer chains and attachment of biomolecules on specific sites thereon). But it is understood that polymer chain synthesis and attachment of biomolecules can also be carried at different times, i.e. synthesis of the biomolecules followed by fixation to the nanoelectrodes.

The measurement of the electrical conductivity before and after deposition of the insoluble essentially electrically insulating precipitate on the nanoelectrodes is essentially carried out by two different methods:

The first one, also termed as "cinetic measurement" measures the electrical conductivity before the addition of the essentially insoluble soluble species, i.e. before the catalysis reaction takes place and after the deposition of the insoluble precipitate. The measurement is carried out at continuous time intervals, which have the same or a different interval period, starting from the beginning of the addition of the essentially insoluble species until the termination of the precipitation, following the reaction over time. Therefore the difference in electrical conductivity before and after precipitation is measured.

The second method makes use of a "negative" reference electrode which usually consists of a planar circular or rectangular metallic layer, for example made of gold. The metallic layer is usually a part of the array of locations (or "spots"), usually all of them consisting of one or more metallic layers where the nanoelectrodes are attached to. The conductivity of this "naked" reference electrode is compared to the conductivity of a spot with nanoelectrodes after deposition of the precipitate on the nanoelectrodes. It is understood that also more than one reference electrode may be present.

In another specific embodiment of the present invention the precipitate is coloured. The coloured precipitate is therefore additionally detectable by optical means like colorimetry, UV/VIS absorption spectroscopy and the like which may yield supplementary information on for example hybridisation or interaction events than solely relying on electrical measurements.

The insoluble, preferably electrically insulating precipitate interacts electrostatically with the nanoelectrodes by blocking the free mobility of the flexible nanoelectrodes. The conformation of the nanoelectrodes is in this case considered as "frozen". This interaction results in a decrease of the flexibility of the nanoelectrodes chains. This decrease in the flexibility of the nanoelectrodes is correlated to a corresponding decrease in their conductivity which can be measured by techniques essentially known to an artisan.

Preferably, the change in conductivity of the nanoelectrodes is detected by a method selected from the group consisting of amperometric measurements, differential pulse voltammetry, impedance spectroscopy and chronoamperometry. Especially preferred is cyclic voltammetry which allows the use of an equipment which is cheap and easy to operate. In general, the choice of the appropriate measurement method depends on the desired application and sensitivity.

Cyclic voltammetry and chronoamperometry are for example preferred if an equipment with small size, cheap system compounds and an easy handling is required. Cyclic voltammetry is preferred when the nanoelectrodes are polymer chains, incorporating an electron donor species. The electron donor species may be either an integral part of the polymer chain or attached thereto. Impedance spectroscopy will be the method of choice if an extremely sensitive method is required.

Impedance spectroscopy yields information on the conductivity of the system investigated. Cyclic voltammetry, or voltammetry in general examines the electrochemical reactions involved.

When the system to be examined changes its conductivity, like for example by influencing the conductivity of the nanoelectrodes consisting essentially of polymer chains, impedance spectroscopy is preferred.

It is especially preferred that the catalytic active moiety is a biocatalyst. Biocatalysts are preferably enzymes which display a wide variety with respect to their chemical nature, structure and reactions to be catalyzed. Thus they can be tailored and selected according to the specific needs. Furthermore, enzymes catalyze a wide variety of biochemical and chemical reactions without being consumed.

Non limiting examples for suitable enzymes are for example proteases, oxidases, reductases and dehydrogenases. Preferred are peroxidases. Especially preferred are alkaline phosphatase, glucose oxidase, acetylcholine-esterase and horseradish peroxidase.

In a further preferred embodiment, the tag comprises further a biotin/streptavidin or biotin/avidin complex. This is due to the fact, that the binding couple biotin-avidin or streptavidin has been investigated in considerable details (see for example Livnah, O.; Bayer, E. A.; Wilchek, M.; Sussman, J. L. *Proc. Natl. Acad. Sci. U.S.A.* 1993, 90, 5076-5080). It appears that the strength of the binding interaction is primarily enthalpy driven. Biotin is easily introduced in biomolecules like oligonucleotides, peptides and the like. Also an enzyme is easily coupled to the peptide skeleton of avidin or streptavidin. The couple biotin/avidin or biotin/strepatividin with its strong binding force is then formed in a much more convenient way than to introduce the enzyme directly to the target biomolecule. The latter way is often tedious, has low yields and does not offer the possibility to choose a large variety of different enzymes. This is much better achieved by the present invention.

In a preferred embodiment of the present invention, one single probe biomolecule is attached to each nanoelectrode. Thereby an enhanced flexibility of the nanoelectrodes is obtained. The precipitation of the detection species results in a significant reduction of their flexibility depending on the nature of the nanoelectrodes, more specifically of the polymers used. This may even result in a total immobilization of the polymer chains. The significant decrease in flexibility results therefore in a corresponding sharp decrease in their electroconductivity. This decrease is easy to detect and allows a more accurate measurement with enhanced sensitivity.

In another preferred embodiment, at least two probe biomolecules are attached to each nanoelectrode. The probe biomolecules may be the same or different from one another. It is understood that also a plurality, i.e. more than two of identical or different probe biomolecules are attached to one nanoelectrode. In still another embodiment a plurality of probe molecules are attached. The more probe biomolecules are attached to each nanoelectrode the more precipitate will be formed. The less significant decrease due to decreased flexibility of the nanoelectrodes provided with a plurality of probe biomolecules is compensated by an increase in detectable precipitate which enhances the sensitivity.

The term "biomolecule" as used herein means any biological molecule in the form of a polymer, such as oligonucleotides, amino acids, peptides, proteins, carbohydrates, antibodies, etc. The term "nucleoside" as used herein comprises both deoxyribonucleosides and ribonucleosides. The term "oligonucleotide" refers to an oligonucleotide that has deoxyribonucleotide or ribonucleotide units. The term thus comprises DNA, RNA, LNA, PNA and chimeras thereof. In the context of the present invention especially preferred biomolecules are oligonucleotides, polypeptides and carbohydrates.

It is preferred that the probe biomolecule further comprises an electron-donor moiety (EDM). The presence of an EDM enhances the electroactivity of the electrically conducting polymer. In especially preferred embodiments of the invention the EDM comprises a transition metal sandwich complex, like substituted or unsubstituted ferrocene, ruthenocene, nickelocene, cobaltocene and the like. These complexes are easy to synthesize and easy to functionalize which facilitates a fixation to the probe biomolecules.

In a further preferred embodiment, the nanoelectrodes, i.e. usually the polymer or copolymer chain, comprise an electron-donor moiety (EDM). The EDM is either part of the polymer chain (backbone), i.e. incorporated in the chain as "chain member" if the EDM is for example bifunctional, i.e. comprising two functional groups or attached thereto if the EDM is monofunctional, i.e. comprising one functional group.

It is further preferred that the solid support is electrically conductive. In another embodiment, the support comprises an electrically insulating layer or consists essentially of an electrically insulating material as for example a plastic material which is covered at least partially with an electrically conductive layer. The support is in another embodiment a semiconductor material comprising an electrically insulating layer, providing preferably in each case that an electrical connection can be established with an electric controlling device unit, preferably via spatially different locations or "flat" two-dimensional metallic electrodes ("spots") which form a so-called "array" of spots on the surface of the support.

In an especially preferred embodiment of the invention, the target biomolecule is an oligonucleotide (DNA or RNA) comprising a segment which is partially on totally complementary to the probe molecule which is also an oligonucleotide. The probe oligonucleotide may contain alpha nucleotides analogous to natural nucleotides and which can be produced on automatic synthesizers. The target oligonucleotides may be double stranded DNA, single stranded DNA, a DNA-RNA hybrid or RNA (ribosomal or messenger). Of course, in the case of double stranded or hybrid oligonucleotides, it should be denatured before carrying out the detection method according to the invention using well-known sandwich hybridisation techniques.

In specific preferred embodiments, the tag further comprises a first detection species, which is especially an oligonucleotide sequence. It is still further preferred that the oligonucleotide comprises a segment which is partially complementary to the target biomolecule. Therefore, target molecules which cannot be tagged by conventional or convenient techniques can be tagged indirectly.

It is especially preferred that the soluble detection species is selected from the group consisting of 5-Bromo-4-chloro-3-phosphate-1H-indole (BCIP), nitrobluetetrazoliumchloride (NBT), dimethylbenzidine, diaminobenzidine, 4-chloro-naphthol, 3-amino-3-ethyl-carbazole and tetramethylbenzidine (TMB). Most preferred is the mixture of BCIP/NBT, where NBT acts as a chromogenic amplifier. Thus, the use of BCIP/NBT offers the possibility of electrochemical and/or optical measurement of the precipitate.

The problem underlying the invention is further solved by a biochip comprising a solid support with a plurality of flexible rod-shaped nanoelectrodes attached to a plurality of spatially different locations on the solid support and probe molecules bound to all or to a plurality of said nanoelectrodes which may be the same or different, a segment of said probe molecules being able to interact specifically with a segment of target biomolecules.

The biochip according to the invention provides a plurality of single "nanoelectrodes", each "nanoelectrode" or a defined number of "nanoelectrodes" bearing one, two or a plurality of probe biomolecules. Preferably the probe biomolecules are selected from the group consisting of oligonucleotides, peptides, proteins, carbohydrates, hormone receptors, lipids. Especially preferred are oligonucleotides.

The biochip according to the invention is preferably used for the detection of nucleic acid sequences of different pathogenic microorganisms, of nucleic acid sequences related to different genetic diseases or of nucleic acid sequences of different tissues.

The present invention relates further to a kit for the detection of target biomolecules in a sample comprising a plurality of biomolecules, comprising:
  a) a support partially functionalized with a plurality of individual nanoelectrodes at various locations on the support and having attached probe biomolecules thereto,
  b) a detection species The term "detection species" in the context of the present invention is synonymous to the additional, essentially soluble species referred to in the foregoing which is transformable in an insoluble precipitate.

Definitions and Abbreviations

In the following, the terms and definitions as used herein are explained for the further illustration of the present invention.

The term "to detect" or "detection" as used herein refers to a qualitative and quantitative determination and identification of target molecules in the sample by electrical or optical measurement techniques.

The term "biomolecule" refers to any molecule existing in nature or artificially synthesized according to a matrix existing in nature, and comprises for example antibodies, proteins, peptides, nucleic acid sequences, i.e. polynucleotides or oligonucleotides comprising at least two deoxyribonucleotides or ribonucleotides, optionally comprising at least one modified nucleotide for example a nucleotide containing a modified base, hormone receptors, lipids, antigenes.

The term "peptide" as used herein refers in particular to any peptide of at least two amino acids in particular a protein, a protein fragment or oligopeptide which is extracted, separated or substantially isolated or synthesized, in particular those obtained by chemical synthesis or by expression in a recombinant organism.

The term "support" denotes any solid three-dimensional body, which does not chemically or physically interact with a sample. The support may be electrically conductive or non electrically conductive.

The term "interacting" as used herein means any interaction between molecular entities, comprising formation of a chemical bond (covalent or ionic), van der Waals interactions, hydrogen bond interactions, adsorption phenomena and the like.

The term "complex" refers to an entity formed by at least two different molecular entities, interacting as specified above. A complex according to the invention is held together by interactions as specified above.

In the following the invention is explained in detail with respect to the figures and the technical description. It is understood that the following examples have illustrative purpose only and are not meant to restrict the scope of the invention.

FIG. 1 shows a substrate 101, for example made of a metal or a metal alloy (e.g. copper, silver, silicon coated with gold, silicon coated with copper, etc.). Substrate 101 carries a plurality of nanoelectrodes 102 which are attached to the substrate 101 via covalent linkages. The nanoelectrodes are preferably individual polymer chains which are regularly or irregularly arranged and have the same or a different length. In a preferred embodiment they are regularly arranged and form a "brush" where the nanoelectrodes have essentially the same length. Preferably, the polymer for the nanoelectrode is a polypyrrole, polymer linked preferably via its 2, 3 or 1 position to the surface. In another embodiment of the invention, another electrically conductive polymer as polypyrrole (and its substituted derivatives) can be used, for example, polythiophene, polyaniline, polytetrahydrofuran their substituted derivatives and the like. The monomeric building blocks of the homopolymers are linked via their respective 3 or 1 positions. It is understood, that also copolymers of different monomeric building blocks as mentioned in the foregoing are comprised within the scope of the invention. With respect to the substituents it is evident that a person skilled in the art will choose the substituents according to the degree of electrical conductivity required.

Furthermore, the nanoelectrodes may comprise, i.e. incorporated into the polymer chain or attached thereto one or more electron donor moieties (EDM), preferably transition metal complexes like metallocenes as ferrocene, nickelocene and the like as specifically described in the foregoing.

In a further embodiment of the present invention, the nanoelectrodes consisting of polymer chains, were obtained by copolymerizing three different components, namely, a) 3 hydroxypyrrole, b) ferrocene linked to 3 hydroxypyrrole and c) an oligonucleotide linked to 3 hydroxypyrrole, thereby generating three different segments in each polymer chain. When considering the plurality of all polymer chains, the three different segments of the plurality of the nanoelectrodes can be considered as forming three "layers" on a spot, if the segments are at each nanoelectrode in the same or at least in essentially the same position.

A biomolecule 105, for example an oligonucleotide, carrying a linker 104 and a complementary segment 103 is fixed via linker 104 onto the polymer chain 102. The attachment is achieved via the formation of a chemical bond between the probe biomolecule and the polymer chain by methods essentially known to a person skilled in the art.

For effecting the detection of a target biomolecule the substrate 101 with probe biomolecules 105 fixed to a plurality of polymer chains 102 is brought in contact with a target molecule 106. The target biomolecules are contained within a solution, dispersion, emulsion and the like. Prior to contacting the target biomolecule 106 with the biochip, the target biomolecule 106 undergoes a reaction with a detection biomolecule 107 whereby the target biomolecule 106 and the detection biomolecule 107 have complementary sections capable of undergoing chemical or physical interactions with each other. It is preferred that the target biomolecule 106 and the detection molecule 107 are oligonucleotides having complementary sequences. The detection biomolecule 107 further comprises a tag 109 which is preferentially biotin. Biotin is linked to the detection biomolecule 107, preferably by a chemical covalent bond. It is understood that in another specific embodiment, the use of detection biomolecule is not necessary. In this case, the tag is directly fixed to the target biomolecule.

Figure 1A:
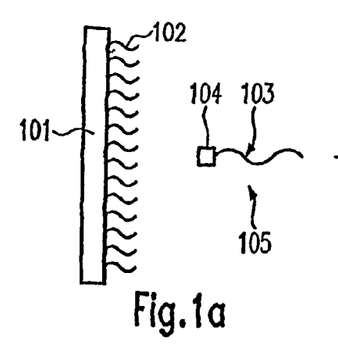
FIG. 1 shows an embodiment of the method according to the invention.
Figure 1B:
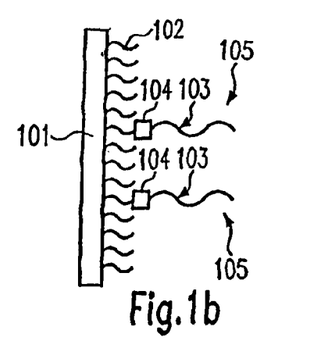
Figure 1C:
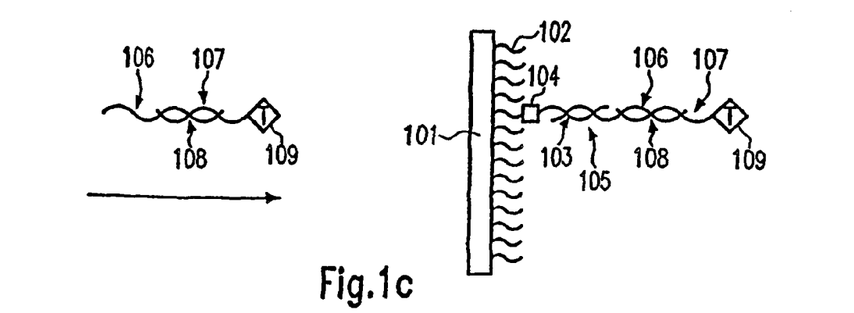
Figure 1D:
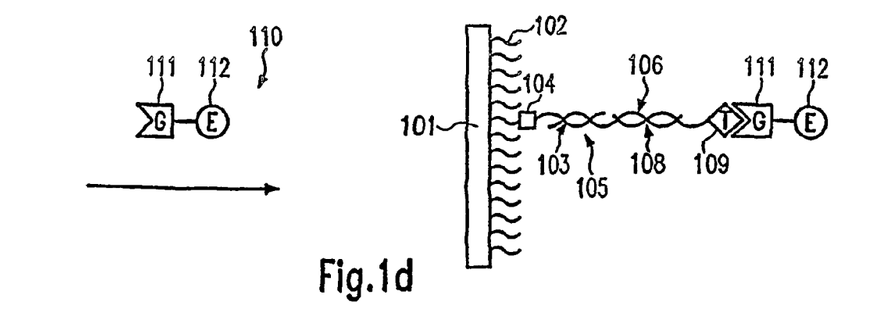
Figure 1E:
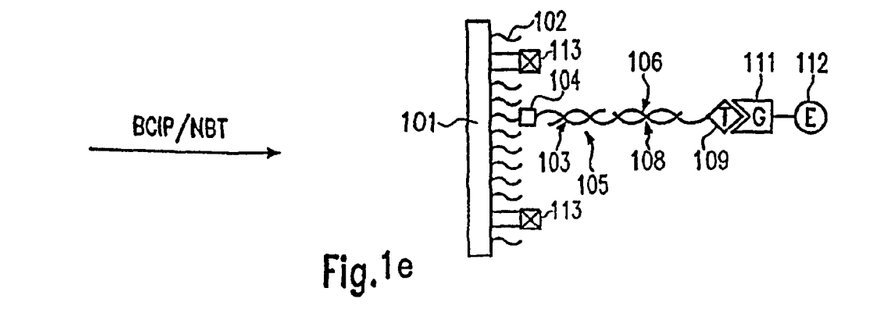

Probe biomolecule 105 and target biomolecule 106 together with the detection biomolecule 107 form a recognition complex as shown in FIG. 1c. The recognition complex 1c is then reacted with a signal-generating agent 110 comprising a tag-binding portion 111 which, for example, may be avidin or streptavidin. The tag 110 further comprises a biocatalyst 112 which is for example alkaline phosphatase, but any other catalyst of enzyme as mentioned in the foregoing section suitable for the purpose of the invention can alternatively be used.

Biotin 109 and streptavidin 111 will form the biotin-streptavidin complex, thereby attaching the catalytic active species 112 to the recognition complex.

Subsequent reaction with BCIP/NBT leads to an oxidation of BCIP and reduction of NBT. Oxidized BCIP/NBT precipitates as precipitate 113 onto the polymer chain 102 of the biochip. The polymer chains are conformationally rigid ("frozen") and immobile after the precipitation of BCIP/NBT 113. The fixation leads to a change of their electroconductivity which can be detected by conductivity measurements as mentioned in the foregoing.

In another embodiment different couples of enzymes and signal generating agents are used. These couples include but are not limited to For example, horseradish peroxidase together with 4-chloro-1-naphthalene, alkaline phosphatase and derivatives of indolylphosphate, glucoseoxidase and tetrazolium salts.

The measurement of the change in electro-conductivity of the polymer chains 102 is carried out by impedance spectroscopy, cyclic voltammetry and the like.

Figure 2:
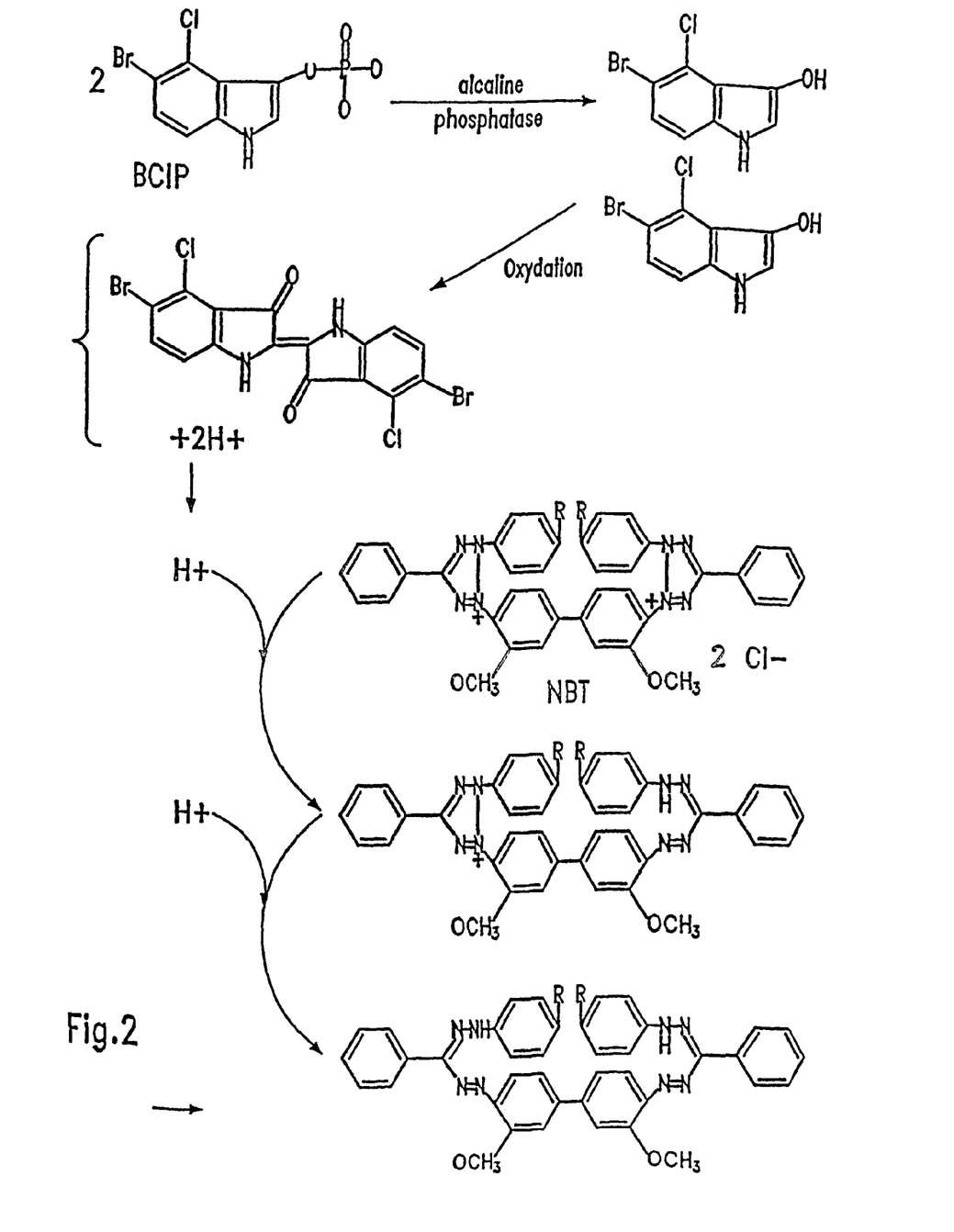
FIG. 2 shows a diagram of the chemical reaction of the detection species upon reaction induced by the catalytic active species.

FIG. 2 shows the redox reaction of the detection species BCIP/NBT under the influence of alkaline phosphatase. After oxidation and addition of acid protons, a coloured tetrameric product NBT is obtained which has an intense colour absorbing at 530 nm. NBT is precipitating on the polymer chains 102 and can also be detected via colorimetric or UV/VIS measurements.

FIG. 3 shows two embodiments of how to attach a oligonucleotide probe biomolecule onto a nanoelectrode consisting of a polymer chain comprising pyrrole units.

Figure 3A:
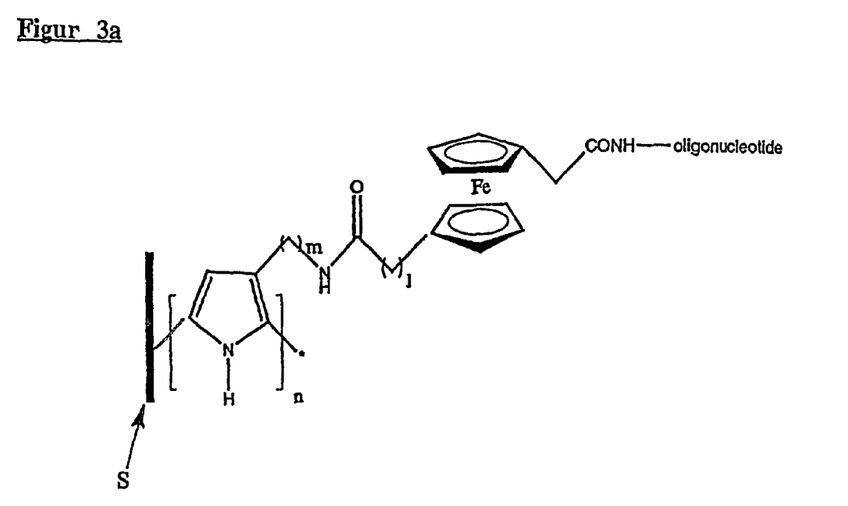
FIG. 3 shows two embodiments according to the invention for the incorporation of probe biomolecules into a nanoelectrode consisting of a polymer chain.

FIG. 3a shows a substrate S. Attached to substrate S, for example a gold-coated silicon comprising substrate, are 3 linked polypyrrole chains. Further a ferrocene moiety is attached to the polymer via a suitable linker. One cp moiety of the ferrocene bears an acyl group substituent which can be modified to attach the oligonucleotide probe molecule thereto. But any other suitable substituents other than acyl are also comprised within the scope of the invention. The letters n and l are integers from 1 to 4. As shown in FIG. 3a one single probe biomolecule is attached to each monomeric building block, i.e. to each pyrrole unit of the polymeric chains.

Figure 3B:
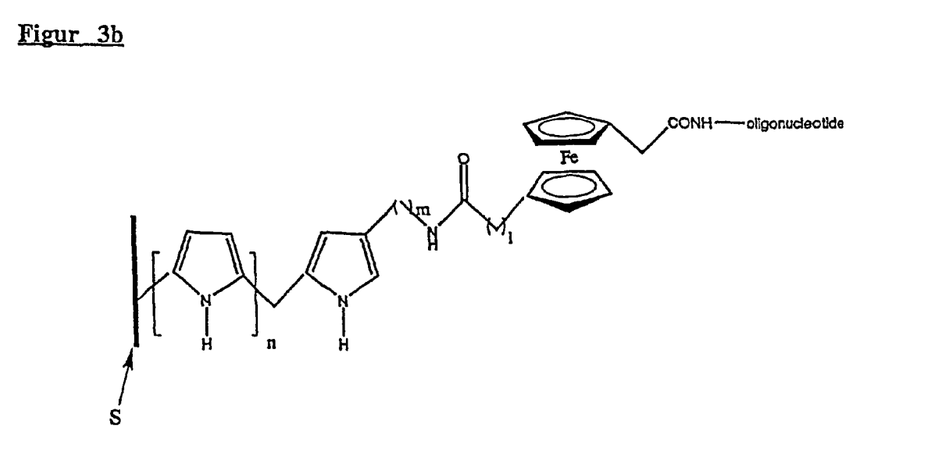

FIG. 3b shows another embodiment for attaching an oligonucleotide probe biomolecule, to a 3 linked polypyrrole chain. As shown in FIG. 3b, only one oligonucleotide probe biomolecule is attached to each polymer chain.

Figure 4:
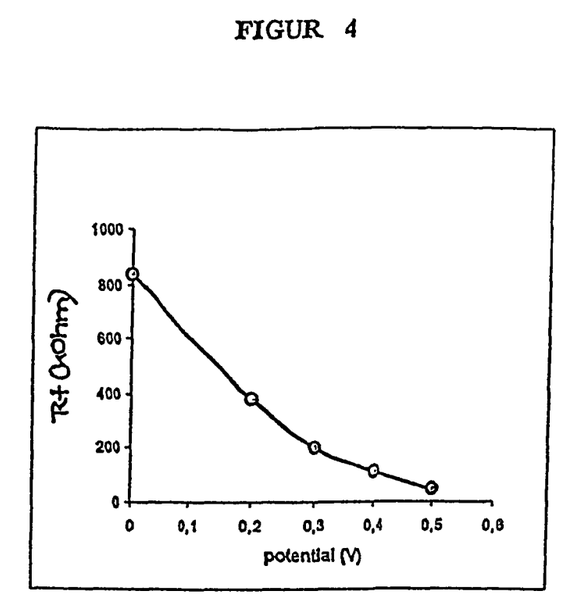
FIG. 4 shows the influence of the oxidation state of nitrogen functionalized PPy/PPy-ODN nanoelectrode polymer chains on their conductivity.

FIG. 4 shows the evolution of the resistance of the charge transfer ($R_t$) through the nanoelectrode, functionalized in the nitrogen position as a function of the potential applied on the nanoelectrode. This resistance decreases when the applied potential increases towards positive values. This is an indication that the more the polymer chains are oxidized the more they are conductive. For a potential of +0.5 V the resistance $R_t$ decreases eight times when compared to an applied potential of 0 V. Consequently, the electrically conductive or semi-conductive polymer nanoelectrodes form in one aspect a matrix for the immobilization of oligonucleotides on the solid support and form in another aspect a transducer where the intrinsic conductivity can be modulated.

Figure 5:
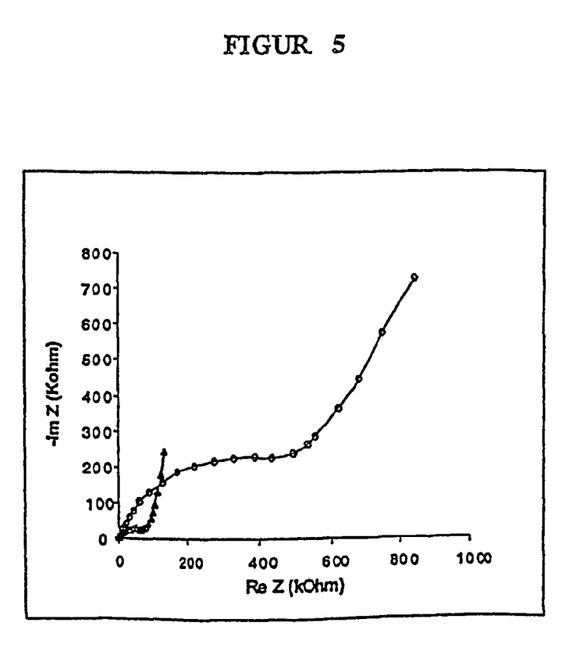
FIG. 5 shows the influence of the length of nitrogen functionalized PPy/PPy-ODN nanoelectrode polymer chains on its conductivity.

FIG. 5 shows the influence of the length of the polymer nanoelectrode PPy/PPy-ODN (polymers are functionalized in their nitrogen position) on the conductivity as a Nyquist diagram (imaginary part of the impedance as a function of their real part). Curve 1 displays the measurement on a nanoelectrode with a length of 80 nm and Curve 2 a nanoelectrode with a length of 160 nm. As be can be seen from FIG. 5, it appears that the conductivity is ten times higher when the length of the nanoelectrodes is 160 nm with respect to a length of 80 nm. Therefore, the longer the nanoelectrodes are (up to approximately 200 nm) the more conductive they are. The ionic conductivity increases when the length increases. However, from a certain length (approximately from 200 nm) the electronic conductivity decreases which forms the limiting factor for increasing the conductivity. Therefore, it is possible to shape the conductivity of the polymer nanoelectrodes in varying their length.

Figure 6:
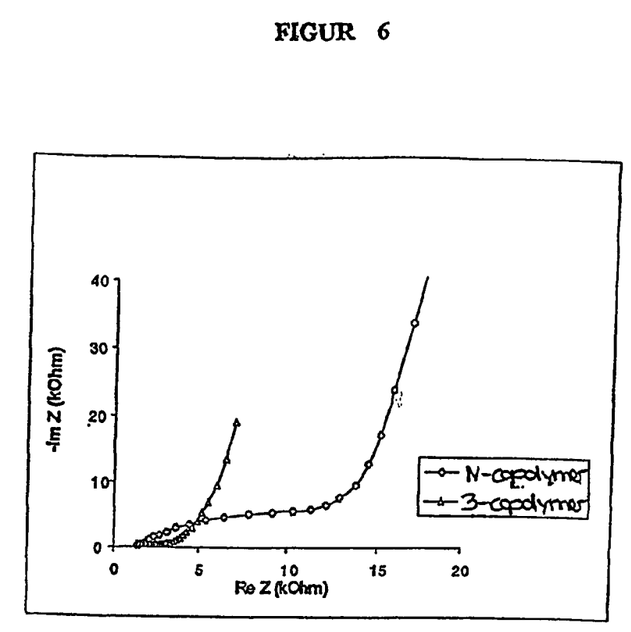
FIG. 6 shows the influence of the position of functionalization (N-functionalization vs 3 functionalization on the conductivity of the nanoelectrode consisting of polymer chains (length 180 nm)

FIG. 6 shows the difference as a Nyquist diagram for a nitrogen functionalized copolymer nanoelectrode and for a 3 functionalized copolymer nanoelectrode. Curve 1 shows a copolymer functionalized in N-position and curve 2 shows a copolymer functionalized in 3 position. The conductivity is six times higher due to a functionalization in 3 position of the oligonucleotide with respect to a nitrogen functionalization. Therefore, it is especially preferred to fix the oligonucleotides on the 3 position on the pyrrolic monomers if it is preferred to work with transducers which are more conductive.

Figure 7:
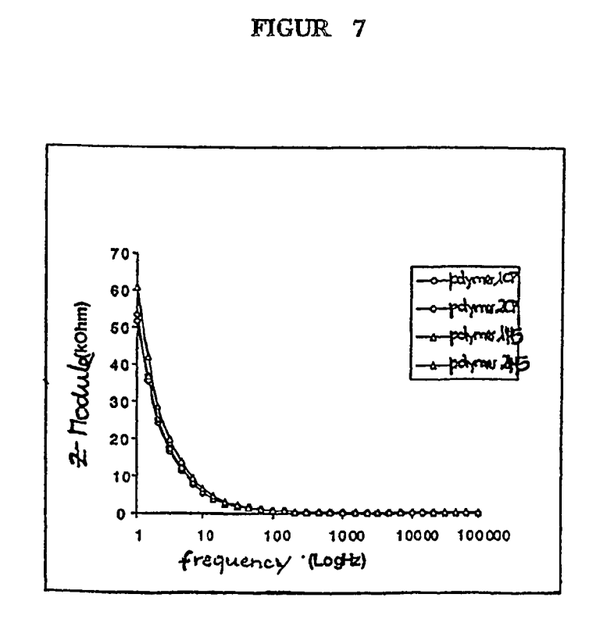
FIG. 7 shows the stability of the responses of impedance measurements for nanoelectrodes consisting of copolymers PPy-OH/PPy-CP and PPy-OH/PPy-M5, functionalized in 3 position, before hybridization and precipitation.

FIG. 7 shows the stability of the impedance responses (Bode diagram, which show the impedance module as a function of a frequency) of 3 functionalized copolymer nanoelectrodes PPy-OH/PPy-CP and PPy-OH/PPy-M5 before hybridization and precipitation. The responses which are obtained are identical and perfectly stable.

Figure 8:
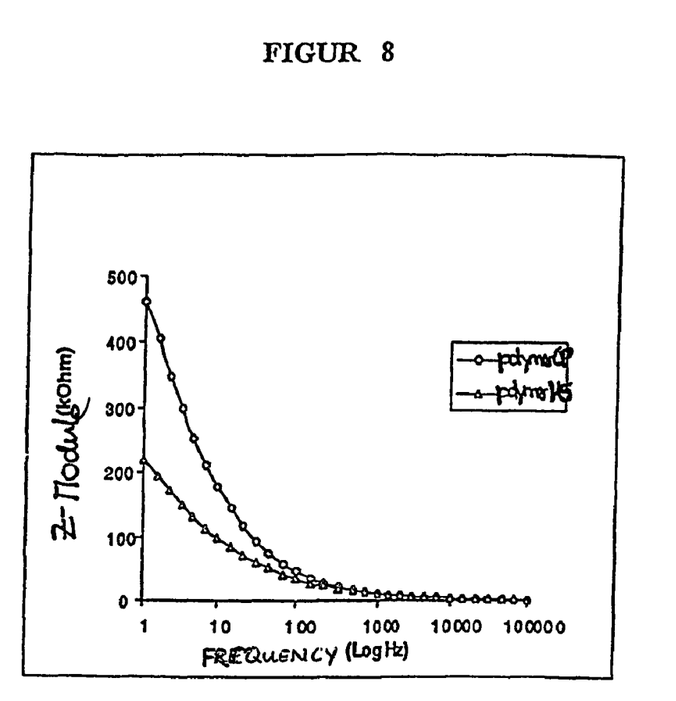
FIG. 8 shows a comparison of the curves of the response of the polymer nanoelectrodes comprising a polymer chain functionalized in 3 position, PPy-OH/PPy-CP (curve 1) vs PPy-OH/PPy-M5 (curve 2), with a chain length of 120 nm, after hybridization (with CP-bio) and precipitation.

FIG. 8 shows a Bode diagram of nanoelectrodes consisting of nanoelectrodes consisting of 3 functionalized copolymer PPy-OH/PPy-CP and PPy-OH/PPy-M5 with a length of 120 nm with and without precipitate of the target with a target concentration of [target]=1 nM. The curves are a function of the frequency in Hz with respect to the impedance module Z. Curve 1 shows the impedance response with precipitate and curve 2 the impedance response without precipitate. As can be seen from FIG. 8, at low frequencies (1-100 Hz) the difference of the response with and without precipitate is considerable. The module Z is approximately two times higher with precipitate. FIG. 8 demonstrates clearly the high sensitivity of the method in connection with the substrate. It is therefore possible to differentiate unambiguously between positive spots (CP in this example) and negative spots (M5) by impedance techniques.

Figure 9:
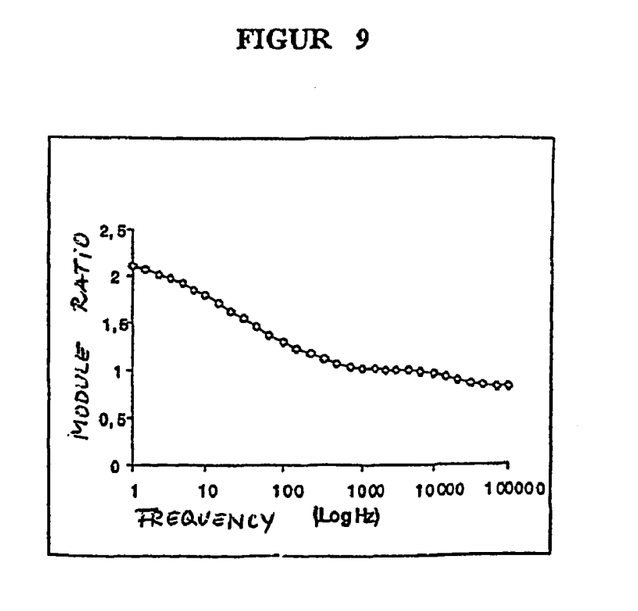
FIG. 9 shows the ratio of the impedance modules of the nanoelectrodes PPy-OH/PPy-CP and PPy-OH/PPy-M5 functionalized in 3 position (Chain length of 120 nm; [target]=1 nM)

FIG. 9 shows the ratio of impedance modules of polymer nanoelectrodes PPy-OH/PPy-CP and PPy-OH/PPy-M5, functionalized in 3 position, with a length of 120 nm. The concentration of target molecules was 0.1 nM. The ratio between those modules is in the range of two with a frequency of 1 Hz and for a nanoelectrode length of 120 nm. It is also evident from the example in FIG. 9, that the frequency influences the sensitivity of the detection.

Figure 10:
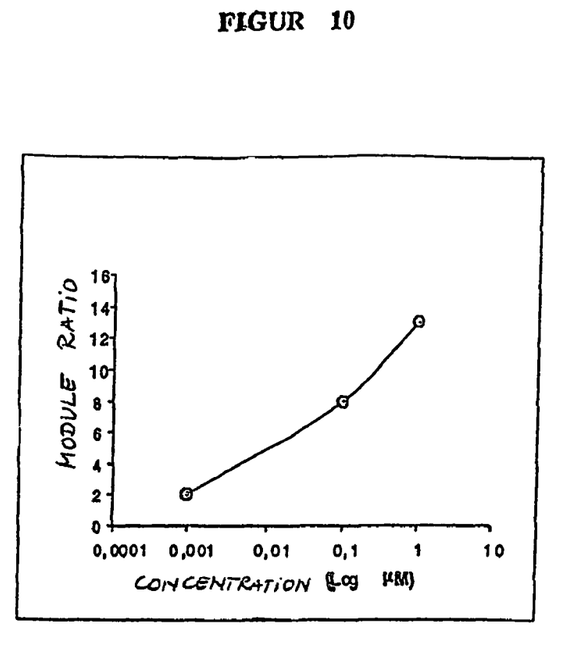
FIG. 10 shows the sensitivity of the impedance spectroscopy measurement as a function of the concentration of target molecules

FIG. 10 shows the sensibility of the impedance measurements as a function of the concentration of target molecules. The concentration (log μM) is a function of the ratio of the impedance modules of the nanoelectrodes PPy-OH/PPy-CP and PPy-OH/PPy-M5, functionalized in 3 position. Measured with a concentration of target concentration of 0.1 μM the ratio of the impedance modules is 8 and with a concentration of 1 nM of target molecules the ratio of the impedance modules is 2.

Conclusion: For a concentration of target oligonucleotides of 1 nM, the ratio of the impedance module at a frequency of 1 Hz is 2. Therefore, this technique allows to decrease the concentration of a target oligonucleotides in the range of $10^3$ before approaching at the detection limit which is obtained at a factor 1 of the ratio of the modules of the CP and M5.

Figure 11:
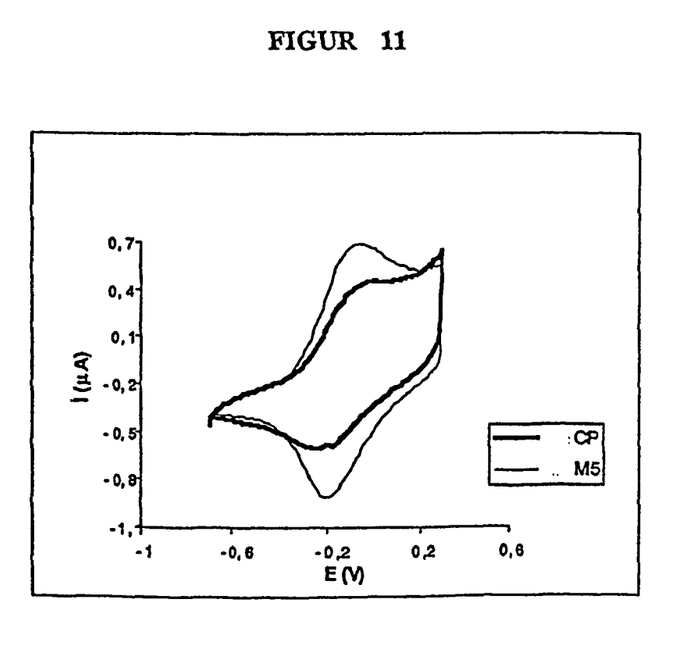
FIG. 11 shows the response of voltamperometric measurements of the nanoelectrodes PPy-OH/PPy-CP (curve 1) and PPy-OH/PPy-M5 (curve 2), functionalized in 3 position, after hybridization with CP-bio and precipitation of BCIP/NBT (length of the nanoelectrode: 50 nm)

FIG. 11 shows two voltamperograms relating to a nanoelectrode consisting of a 3 functionalized copolymer PPy-OH/PPy-CP after hybridization and precipitation and on the other side on a negative control nanoelectrode consisting of a copolymer PPy-OH/PPy-M5 functionalized in its 3 position. The concentration of target CP-bio was 1 nM. The measured intensity of the oxidation peak of the response of the nanoelectrode PPy-OH/PPy-CP (3) is weaker than those of the nanoelectrode PPy-OH/PPy-M5 which has no precipitate. The ratio of the intensity of the oxidation peak of the CP and M5 nanoelectrodes at a potential of −50 mV which is about 1.6. The same holds for the reduction peak which is situated at around −180 mV. Therefore, this electrochemical technique allows also to differentiate between positive nanoelectrodes (CP) and negative nanoelectrodes (M5).

Figure 12A:
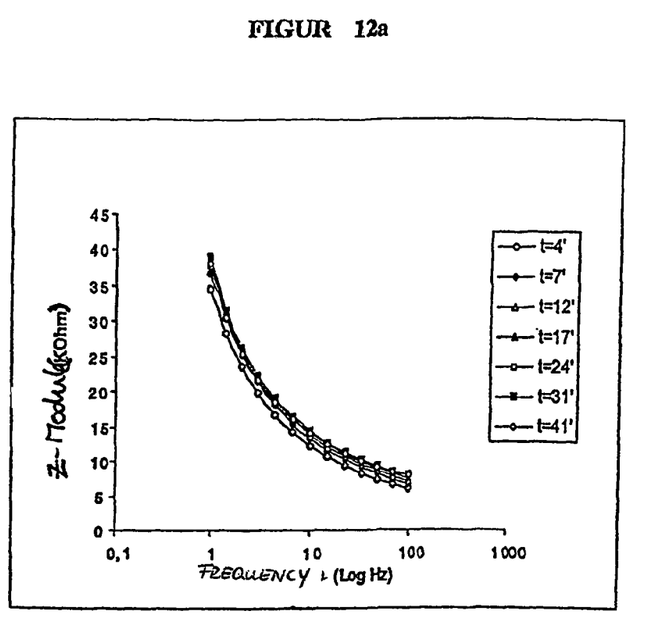
FIG. 12a shows the response of impedance spectroscopy measurement of a negative sample with the nanoelectrode PPy-OH/PPy-M5 functionalised in 3 position during precipitation of BCIP/NBT into PPy-OH/PPy-CP. (cinetic measurement)

FIG. 12 a shows impedance measurements on the buffer of the substrate. This allows to follow the evaluation of the precipitation reaction during the reaction time. On the nanoelectrode consisting of the copolymer PPy-OH/PPy-M5 (3) where no hybridization took place, the Bode diagram which shows the impedance module as a function of the frequence develops with respect to the reaction time only slightly. The conductivity of the polymer nanoelectrodes is therefore not altered.

Figure 12B:
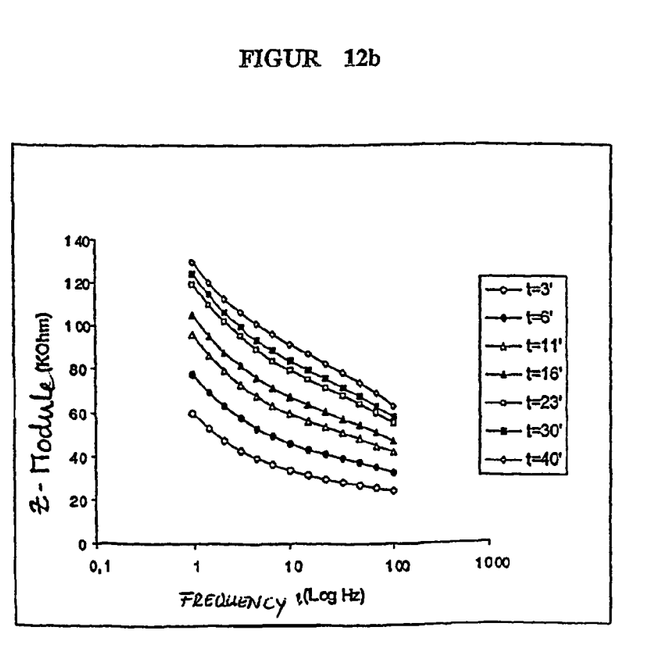
FIG. 12b shows the response of impedance spectroscopy measurement during precipitation of BCIP/NBT on nanoelectrodes consisting of the copolymer PPy-OH/PPy-CP functionalised in 3 position. (cinetic measurement)

FIG. 12 b shows the change in electrical conductivity in a Bode diagram during the precipitation of BCIP/NBT on polymer nanoelectrodes of a 3 functionalized copolymer PPy-OH/PPy-CP. The curve diagram of FIG. 12 b is a function of the frequency in Hz versus the impedance module in kHz. The concentration of target molecules was 1 nM (CP-bio) and the length of the nanoelectrodes was 180 nm.

With the 3 functionalized copolymer nanoelectrode PPy-OH/PPy-CP where a hybridization took place, the curve obtained as of the impedance module as a function of the frequency develops during time of about 40 minutes. For every frequency in the range between 1 and 100 Hz, the value of the module doubles during this reaction time. This increase is related to the cinetic of the precipitate formed on the nanoelectrode as a consequence of the hybridization of the oligonucleotide.

EXAMPLES

| Abbreviations and Definitions | |
|---|---|
| ECS: | saturated calomel electrode (reference electrode) |
| CP: | oligonucleotide for positive control with the following sequence: |
| | 5' TTT TTT TTT TGC CTT GAC GAT ACA GCT A 3' |
| CP-biotin (CP-bio): | complementary biotinylated oligonucleotide of CP with the following sequence: |
| | 5' biotin - T AGC TGT ATC GTC AAG GCA 3' |
| M5 | oligonucleotide for negative control; with the following sequence: |
| | 5' TTT TTT TTT TTT GGA GCT GCT GGC G 3' |
| M5-biotin (M5-bio) | complementary biotinylated oligonucleotide of M5; with the following sequence: |
| | 5' biotin-C GCC AGC AGC TCC AAA 3' |
| ODN | oligonucleotide |
| TH1X | TH1X is a buffer solution consisting of <13.3 g/l, $Na_2HPO_4$, 29, 22 g/l NaCl, 20 g/l PEG 4000, 6.5% Tween 20, 1 g/l gelatine, 14% DNA of herring sperm 10 mg/ml sonicated |
| TR: | TR is a rinsing buffer consisting of: 8 g/l of NaCl; 0.2 g/l of KCl; 0.76 g/l of $Na_2HPO_4$; 0.19 g/l of $KH_2PO_4$; 0.5% of tween 20; 1 mM of EDTA. |
| PAL | alcaline phosphatase |
| BM purple AP substrate | chromogenic substrate for alcaline phosphatase, (Roche Applied Substrate) |
| CV | Cyclic voltammetry |

The electrochemical cell used in the following example 2 is a Micam cell with a volume of 1 ml with a platinum counter-electrode (diameter: 4 mm). The overall setup has 3 electrodes. For the example 3, no electrochemical cell was used. A droplet of 50 μl of electrosynthesized solution is applied onto the biochip which had an integrated reference electrode and a counter-electrode.

Example 1

1. Electropolymerisation of nitrogen functionalized polypyrrole to yield nanoelectrodes: All copolymers are electro-synthesized with an applied potential of +1V versus (ECS) from an aqueous solution of $LiClO_4$ 0.1 M containing 20 mM of pyrrole monomers and 5 μM of a pyrrole oligonucleotide monomer (CP or M5). The polypyrrole homopolymer was also electro-synthesized with an applied potential of +1V versus ECS from a 20 mM solution of pyrrole. A Micam cell was used as the electro-chemical cell.

9 spots in a circular arrangement (OLISA™) consisting of metallic circles of a gold layer on each biochip consisting essentially of a plastic material were provided with the polymer nanoelectrodes. The spots are connected by usual means to external control units.

4 spots with chains of copolymers of polypyrrole/polypyrrole-CP (Qs=55 μC; Qs=70 μC; Qs=40 μC; Qs=100 μC), four spots of co-polymer of polypyrrole/polypyrrole-M5 (Qs=55 μC; Qs=70 μC; Qs=40 μC; Qs=100 μC) and one spot of a polypyrrole homopolymer without probe biomolecule (Qs=60 μC) were synthesized. After deposition of the polymer nanoelectrodes on each spot, the electro-chemical response of each polymer was measured by cyclic voltrammetric measurements (CV) in an aqueous solution of 0.1 M $LiClO_4$ by changing the potentials between −0.2 V and +0.6 V versus ECS. Each spot was afterwards analysed with a hybridization buffer.

Hybridization

The hybridization of the M5 probes was realised by incubating the biochip in a solution comprising target ODN M5 biotin with a concentration of 0.5 μM for 30 min.

Each spot was afterwards analysed via VC with a hybridization buffer by changing the potentials between −0.2 V and +0.6 V versus ECS.

After measurement of each spot, the biochip is washed four times with a washing buffer.

On each spot a droplet of a streptavidin alkaline phosphatase solution (PAL) which was diluted to $100^{th}$ was added. The biochip was left standing for 5 min. at room temperature. Afterwards the biochip was washed four times with the wash buffer.

Precipitation:

On each spot a droplet of a solution of BM purple AP substrate was applied. The biochip was left for one hour (incubation) at room temperature in darkness. Afterwards the biochip was washed four times with the wash buffer. the wash buffer consisted of 8 g/l NaCI, 0.2 g/l KCI, 0.76·g/l $Na_2H_2PO_4$, 0.19 g/l $KH_2PO_4$, 0.5% Tween 20, 1 µM EDTA. A blue deposit or precipitate appeared on every M5 spot.

Each film was analysed by CV with a new solution of hybridization buffer solution by changing the potentials between −0.2 V and +0.6 V versus ECS.

Example 2

Four biochips each comprising 9 spots were prepared. 4 spots of each chip were provided with copolymer nanoelectrodes consisting of of PPY/PPY-CP functionalized in N position, 4 spots were provided with copolymer nanoelectrodes consisting of PPY/PPY-M5 functionalized in N position. One spot consisted of pure gold only and is the counter electrode.

The synthesis of the electrically conductive polymer nanoelectrodes was performed with an applied potential of +0.9 V vs ECS. The solution for the electrosynthesis of the copolymers was 0.1 M $LiClO_4$ in water containing 20 mM of monomeric pyrrole and 5 µM of a monomeric pyrrole functionalised with oligonucleotide (CP or M5). The electrochemical cell was a Micam cell with three electrodes.

Biochip 1 was synthesized (Qs=20 mC×cm$^{-2}$/spot) with a polymer nanoelectrode length of 40 nm. Biochip 2 was synthesized (Qs=30 mC×cm$^{-2}$/spot) with a polymer nanoelectrode length of 60 nm. Biochip 3 was synthesized (Qs 40 mC×cm$^{-2}$/spot) with a polymer nanoelectrode length of 80 nm. Biochip 4 was synthesized (Qs=10 mC×cm$^{-2}$/spot) with a polymer nanoelectrode length of 20 nm.

Hybridization:

1 µl ODN-biotin (ODN=CP or M5 each at 10 µM) in 99 µl TH1X buffer were incubated for 1 h at 37° C. The final concentration of ODN-biotin was 0.1 µM). Biochip 1 and 3 were incubated with CP-biotin, whereas biochips 2 and 4 were incubated with M5-biotin.

Tagging:

A droplet of 30 µl of streptavidin-PAL complex (0.4 µl of Ci=1 mg/ml) diluted in 30 µl of hybridisation buffer is applied onto each biochip followed by incubation for 5 minutes at ambient temperature and washing with rinsing buffer (TR).

Precipitation

A droplet of 30 µl of BM purple AP substrate solution is applied on each biochip followed by incubation for 45 minutes at ambient temperature followed by washing 4 times with TR.

A blue precipitate appeared on each hybridised spot where a hybridisation reaction took place.

Analysis of the Polymer Nanoelectrodes with Respect to their Average Length

The analysis of the polymer nanoelectrodes of the biochip 1 to 4 was carried out with cyclic voltammetry after precipitation. The electrochemical response of each spot was measured with a scanning speed of 10 mV/s in an aqueous 0.1 M $LiCLO_4$ solution by changing the potential in a range between −0.1 V and +0.5 V vs ECS.

Table 1 shows the influence of the precipitate on copolymer nanoelectrodes consisting of the nitrogen functionalized polymer PPy/PPy-ODN with varying length. Table 1 shows the intensity values of the oxidation peaks of the voltamperametric responses obtained on nitrogen functionalized PPy/PPy-ODN copolymer nanoelectrodes after hybridization and precipitation. The reference measurement is represented by the PPy/PPy-M5 copolymer nanoelectrode where no hybridization took place and consequently no precipitate was formed. A less important intensity in the range of 20-30% is obtained on polymer nanoelectrodes, where hybridization and formation of an isolating precipitate took place. The values show that the length of the polymer nanoelectrode play an important role on the sensitivity of the measurement. Nanoelectrodes were prepared with an average length of 20 nm. Ip oxidation of the non hybridized spot was 35 nA (at E=+0.35 V/ECS), whereas the Ip oxidation of the hybridized spot with precipitate was 27 nA (at E=+0.35 V/ECS).

TABLE 1

| | Polymer nanoelectrode length of N-functionalized PPy/PPy-ODN polymers | | | |
|---|---|---|---|---|
| | 20 nm | 40 nm | 60 nm | 80 nm |
| intensity (nA) precipitation hybridised spot | 27 | 33 | 49 | 50 |
| intensity (nA) non hybridised spot | 35 | 45 | 65 | 73 |
| ratio of intensity CP/M5 (%) | 23 | 27 | 25 | 32 |

Table 1 shows also the influence of the precipitate on a copolymer nanoelectrode with an average length of 40 nm. Ip oxidation of the non hybridized spot was 45 nA (at E=+0.35 V/ECS), whereas the Ip oxidation of the hybridized spot with precipitate was 33 nA (at E=+0.35 V/ECS).

Table 1 shows also the influence of the precipitate on a copolymer nanoelectrode with an average length of 60 nm. Ip oxidation of the non hybridised spot was 65 nA (at E=+0.35 V/ECS), whereas the Ip oxidation of the hybridised spot with precipitate was 49 nA (at E=+0.35 V/ECS)

Further, the influence of the precipitate on a copolymer nanoelectrode with an average length of 80 nm is shown in table 1. Ip oxidation of the non hybridised spot was 73 nA (at E=+0.35 V/ECS), whereas the Ip oxidation of the hybridised spot with precipitate was 50 nA (at E=+0.35 V/ECS).

The most important intensity observed for a nitrogen functionalized copolymer nanoelectrode PPy/PPy-CP with respect to a blind copolymer nanoelectrode PPy/PPy-M5 (functionalized in N position) is obtained with polymer nanoelectrodes with a length of 80 nM. In this case, the intensity is around 30% weaker. Therefore, the optimum chain length in the case of a nitrogen functionalized copolymer nanoelectrode is around 50-160 nm, most preferred between 80-120 nM. The formation of an isolating precipitate on the surface of a long polymer nanoelectrode influences the measurement on the polymer nanoelectrodes. The longer the polymer nanoelectrodes are, the more it is easier for the precipitate of being inserted between the long polymer nanoelectrodes and to decrease considerably the ionic conductivity.

It is important to show the influence of the oxidation state of the polymer nanoelectrodes, their length and their structure (position of the functionalization by the oligonucleotides) on their conductivity. The tuning of the conductivity of the polymer nanoelectrodes is one of the major advantages of the present attachment mode with respect to other immobilization methods for oligonucleotides known in the art. FIGS. 4, 5 and show the result of impedance spectroscopy and measurements on a nitrogen functionalized polymer nanoelectrodes PPy/PPy-CP.

Furthermore, the substitution position of the oligonucleotides on the monomeric pyrroles allows also to modulate the conductivity of the resulting polymer nanoelectrodes (FIG. 6). The different possible interactions between the substituents can cause a torsion of the polymer chains. The structure of a 3 functionalized polymer is more favourable for electrical conductivity because the torsion is less important. The electronic transfer to the chain is improved and the conductivity of the 3 functionalized copolymer nanoelectrodes is considerably improved compared to a N functionalized copolymer.

The measurements have been performed in a Faraday cage in order to minimize the ground noise. A filter was used for a stability correction. For each frequency, three measurements have been averaged (Na=3). The applied potential on the electrode can be selected by a person skilled in the art by usual measurements. The selected frequency range is in the order of 100 kHz-0.1 Hz. The amplitude of the sinusoidal entry signed was chosen at approx. 40 mV.

The conductivity of the polymer nanoelectrodes can be improved in increasing the oxidation state of the polymer chains (FIG. 4). The electronic structure of the polymer nanoelectrodes of the polypyrrole type is correlated with the imposed oxidation potential. The mobility of the charges on the conjugated chain of the polymer is increased by an increased oxidation potential. However, the impedance measurements are becoming less stable if the polymer chains are not near their equilibrium potential.

The length of the polymer nanoelectrodes influences the measured impedance. (FIG. 5)

The length of the polymer nanoelectrodes influences the measured impedance in that longer chains result in a decreased impedance measured. This means that longer polymer chains are more electrically conductive than shorter polymer chains.

Example 3

Material:

The polymer nanoelectrodes were electrosynthesized by means of a 50 µl droplet applied on the chip which had an integrated reference and a counter electrode.

As a potentiostat, a four-channel VMP-2 (Bio-logic Grenoble, France) was used, software for chronoamperometry and impedance measurements were: EGG and Bio-logic. Polymer nanoelectrodes were electrosynthesized on a substrate as explained in example 2, with an applied potential of +0.75V/ECS. The solution for the electrosynthesis of the copolymer nanoelectrodes was 0.1 M $LiCLO_4$ in water containing 0.1 M of the pyrrole-OH monomer functionalised in 3 position and 25 µM of the pyrrole-ODN monomer functionalised in 3 position (CP and M5). Four spots with copolymer nanoelectrodes PPY-OH/PPY-CP and four spots with copolymer nanoelectrodes PPY-OH/PPY-M5 were synthesized. The length of the polymer nanoelectrodes on each spot was different.

Hybridization was performed as follows:

Incubation during 1 h at ambient temperature followed by addition of the hybridisation solution

[ODN-bio]1=1 µM or

[ODN-bio]2=0.1 µM or

[ODN-bio]3=1 nM

Marker Procedure:

Incubation for 5 min by room temperature at a droplet of 30 µl of a solution of streptavidin alkaline phosphatase (PAL) (concentration of PAL as 1 mg/ml) that is 0.4 µl of PAL and 30 µl of THIX which yielded 400 ng/droplet on the biochip (8 spots).

Precipitation Procedure:

The position of a solution of BM purple AP substrate on the biochip followed by incubation of 40 min. at room temperature without exposure to light.

After the incubation step, the spots and the biochip were rinsed with a rinsing buffer (TR).

Impedance Measurements:

The impedance measurements were realized on spots for each polymer nanoelectrode of the biochip (four positive spots (CP) and four blind spots (M5) in $LiCLO_4$ 0.1 M after precipitation.

The impedance measurements were realized under the same conditions as indicated in example 2.

FIG. 7 shows the variation in comparing the impedance responses of so-called positive copolymer nanoelectrode where hybridization and precipitation took place and response of those negative calibrating copolymer nanoelectrodes where no hybridization took place. Before hybridization the electrochemical response of both copolymer nanoelectrodes is identical. Therefore, even the attached oligonucleotide sequence (CP or M5) does not influence the conductivity of the polymer nanoelectrodes.

The impedance measurements after hybridization and precipitation (FIG. 8) confirm that the formation of an isolating precipitate on the polymer nanoelectrodes blocks the ionic transfer and the electronic transfer at the interface polymer nanoelectrodes/solution. The conductivity of the polymer nanoelectrode is strongly influenced and this even for a very small quantity of a precipitate which is correlated to a small quantity of hybridized target oligonucleotides. This electrochemical technique is perfectly adapted to the selected system, the precipitation of an isolating substrate, for detecting the hybridization of oligonucleotides. For a nanoelectrode length of about 120 nM the precipitate was found to be inserted considerably in between the individual plurality polymer electrodes and decreases their conductivity.

The variations in the electrical conductivity of the copolymer nanoelectrodes is more important when weak frequencies between 1 and 100 Hz frequencies are used (FIG. 9).

The detection sensitivity is in the order of 1 pM, which is about $10^8$ molecules/mL (FIG. 10).

The impedance measurements can be carried out in the buffer substrate (FIG. 12). Therefore, it is possible to follow the evolution of the precipitation reaction in real time. The detection of the hybridization via cinetic measurement of the precipitation is faster and more liable as the comparative method of the measurement of impedance modules of calibrating copolymer nanoelectrodes and positive copolymer nanoelectrodes.

Also, a cyclic voltamperometric study has been carried out on 3 functionalized copolymer nanoelectrodes for a concentration of a target CP-bio of 1 nM (FIG. 11). The intensity of the measured oxidation peaks on the response of a CP copolymer nanoelectrode is 40% weaker than those measured for the copolymer nanoelectrode M5. This loss in intensity is directly correlated to a decrease of the conductivity of the polymer nanoelectrodes. This is a direct consequence of the formation of an isolating precipitate on the surface of the polymer nanoelectrodes. By this technique, it is therefore also possible to detect and to quantify the phenomenon of hybridization. It is understood, that this technique enables also to quantify assays with proteins or haptens as long as specific ligands are accessible. However, the sensitivity is slightly decreased when compared to impedance spectroscopy. The latter detection technique is therefore preferred due to their ease of use and also for the possibility of a miniaturization of measurement apparatuses.

The invention claimed is:

1. A method for detecting a target biomolecule in a sample comprising a plurality of biomolecules, whereby the target biomolecule is provided directly or indirectly with a tag, which is linked to a signal generating agent comprising a catalytic active moiety which catalyses the transformation of an additional soluble species to an insoluble precipitate, said method comprising the steps of:
   a) providing a solid support with a plurality of spatially different locations arranged on its surface, whereby at least one location is electrically conducting and a plurality of individual flexible nanoelectrodes with probe biomolecule attached thereto being linked to said location,
   b) bringing the sample in contact with the solid support comprising said probe biomolecules, thereby the probe biomolecule and the target biomolecule interacting together,
   c) adding the soluble species,
   d) transforming the soluble species into the insoluble precipitate forming a deposit essentially on or at the nanoelectrodes, thereby decreasing the flexibility of the nanoelectrodes
   e) measuring the electrical conductivity of the plurality of the nanoelectrodes at least one location, wherein a decrease in the flexibility of the electrode causes a decrease in the electrical conductivity to indicate the presence of the target biomolecule.

2. The method according to claim 1, wherein the value for the electrical conductivity obtained in step e) is compared with a value obtained before step e).

3. The method according to claim 2, wherein a change in electrical-conductivity is measured by amperometric measurements, differential pulse voltammetry, chronoamperometry, or impedance measurements.

4. The method according to claim 1, wherein the catalytic active moiety is a biocatalyst.

5. The method according to claim 4, wherein the biocatalyst is an enzyme.

6. The method according to claim 5, wherein the enzyme is oxidases, peroxidases, reductases or dehydrogenases.

7. The method according to claim 1, wherein the tag comprises further a biotin/avidin or biotin/streptavidin complex.

8. The method according to claim 1, wherein the probe biomolecule is oligonucleotides, polypeptides, proteins, antigenes, antibodies, enzymes, receptors or carbohydrates.

9. The method according to claim 1, wherein the probe biomolecule and/or all or a portion of the nanoelectrodes further comprise an electron-donor group.

10. The method according to claim 9, wherein the electron-donor group comprises a transition metal complex.

11. The method according to claim 1, wherein the solid support is electrically conductive or is an insulator deposited on a conductive layer.

12. The method according to claim 1, wherein the target biomolecule is an oligonucleotide comprising a segment which is partially complementary to the probe molecule.

13. The method according to claim 12, wherein the tag comprises is linked to a first detection species.

14. The method according to claim 13, wherein the first detection species is an oligonucleotide.

15. The method according to claim 14, wherein the oligonucleotide comprises a segment which is partially complementary to the target biomolecule.

16. The method according to claim 1, wherein the soluble species is 5-Bromo-4chloro-3-phosphate-1H-indole-(BCIP), nitrobluetetrazoliumchloride (NBT), dimethylbenzidine, diaminobenzidine, 4-chloro-naphthole, 3-amino-3-ethylcarbazole, or tetramethylbenzidime (TMB).

17. A method for detecting a target biomolecule in a sample comprising a plurality of biomolecules, whereby the target biomolecule is provided directly or indirectly with a tag, which is linked to a signal generating agent comprising a catalytic active moiety which catalyses the transformation of an additional soluble species to an insoluble precipitate, said method comprising the steps of:
   a) providing a solid support with a plurality of spatially different locations arranged on its surface, whereby at least one location is electrically conducting and a plurality of individual flexible electropolymerized nanoelectrodes with probe biomolecule attached thereto being linked to said location,
   b) bringing the sample in contact with the solid support comprising said probe biomolecules, thereby the probe biomolecule and the target biomolecule interacting together,
   c) adding the soluble species,
   d) transforming the soluble species into the insoluble precipitate forming a deposit essentially on or at the nanoelectrodes, thereby decreasing the flexibility of the nanoelectrodes
   e) measuring the electrical conductivity of the plurality of the nanoelectrodes at least one location, wherein a decrease in the flexibility of the electrode causes a decrease in the electrical conductivity to indicate the presence of the target biomolecule.

18. A method for detecting a target biomolecule in a sample comprising a plurality of biomolecules, whereby the target biomolecule is provided directly or indirectly with a tag, which is linked to a signal generating agent comprising a catalytic active moiety which catalyses the transformation of an additional soluble species to an insoluble precipitate, said method comprising the steps of:
   a) providing a solid support with a plurality of spatially different locations arranged on its surface, whereby at least one location is electrically conducting and a plurality of individual flexible nanoelectrodes, which nanoelectrodes are optionally substituted polypyrroles or copolymers thereof, with probe biomolecule attached thereto being linked to said location,
   b) bringing the sample in contact with the solid support comprising said probe biomolecules, thereby the probe biomolecule and the target biomolecule interacting together,
   c) adding the soluble species,
   d) transforming the soluble species into the insoluble precipitate forming a deposit essentially on or at the nanoelectrodes, thereby decreasing the flexibility of the nanoelectrodes
   e) measuring the electrical conductivity of the plurality of the nanoelectrodes at least one location, wherein a decrease in the flexibility of the electrode causes a decrease in the electrical conductivity to indicate the presence of the target biomolecule.

19. The method according to claim 18, wherein the nanoelectrodes are electropolymerized.

* * * * *

```
                        SEQUENCE LISTING

<160> NUMBER OF SEQ ID NOS: 4

<210> SEQ ID NO 1
<211> LENGTH: 28
<212> TYPE: DNA
<213> ORGANISM: Artificial Sequence
<220> FEATURE:
<223> OTHER INFORMATION: Description of Artificial Sequence: Synthetic
      CP (oligonucleotide for positive control)

<400> SEQUENCE: 1
tttttttttt gccttgacga tacagcta                                          28

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      CP Biotin (CP-bio)(Complementary biotinylated oligonucleotide of
      CP)
<220> FEATURE:
<221> NAME/KEY: modified_base
<222> LOCATION: (1)
<223> OTHER INFORMATION: biotin-t

<400> SEQUENCE: 2
tagctgtatc gtcaaggca                                                    19

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      M5 (oligonucleotide for negative control)

<400> SEQUENCE: 3
tttttttttt ttggagctgc tggcg                                             25

<210> SEQ ID NO 4
<211> LENGTH: 16
<212> TYPE: DNA
<213> ORGANISM: Artificial Sequence
<220> FEATURE:
<223> OTHER INFORMATION: Description of Artificial Sequence: Synthetic
      M5-biotin (M5-bio)(Complementary biotinylated oligonucleotide of
      M5)
<220> FEATURE:
<221> NAME/KEY: modified_base
<222> LOCATION: (1)
<223> OTHER INFORMATION: biotin-c

<400> SEQUENCE: 4
cgccagcagc tccaaa                                                       16
```